United States Patent
Bukawa et al.

(10) Patent No.: US 9,351,919 B2
(45) Date of Patent: May 31, 2016

(54) COMPOSITIONS CONTAINING SILICON RESIN, OIL AND GELLING AGENT

(71) Applicant: L'OREAL, Paris (FR)

(72) Inventors: Yoriko Bukawa, Chuou-ku (JP); Hy Si Bui, Piscataway, NJ (US); Kimberly Bradshaw, Monmouth Junction, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/363,215

(22) PCT Filed: Dec. 28, 2012

(86) PCT No.: PCT/US2012/072052
§ 371 (c)(1),
(2) Date: Jun. 5, 2014

(87) PCT Pub. No.: WO2013/102065
PCT Pub. Date: Jul. 4, 2013

(65) Prior Publication Data
US 2014/0348769 A1 Nov. 27, 2014

Related U.S. Application Data

(60) Provisional application No. 61/582,087, filed on Dec. 30, 2011.

(51) Int. Cl.
| | | |
|---|---|---|
| *A61Q 1/04* | (2006.01) | |
| *A61K 8/37* | (2006.01) | |
| *A61K 8/25* | (2006.01) | |
| *A61K 8/89* | (2006.01) | |
| *A61K 8/92* | (2006.01) | |
| *A61Q 1/06* | (2006.01) | |
| *A61K 8/81* | (2006.01) | |
| *A61K 8/891* | (2006.01) | |
| *A61K 8/58* | (2006.01) | |
| *A61Q 1/00* | (2006.01) | |
| *A61Q 1/02* | (2006.01) | |
| *A61K 8/02* | (2006.01) | |

(52) U.S. Cl.
CPC ... *A61K 8/89* (2013.01); *A61K 8/25* (2013.01); *A61K 8/37* (2013.01); *A61K 8/375* (2013.01); *A61K 8/585* (2013.01); *A61K 8/8117* (2013.01); *A61K 8/891* (2013.01); *A61K 8/92* (2013.01); *A61K 8/927* (2013.01); *A61Q 1/00* (2013.01); *A61Q 1/02* (2013.01); *A61Q 1/04* (2013.01); *A61Q 1/06* (2013.01); *A61K 2800/10* (2013.01); *A61K 2800/43* (2013.01); *A61K 2800/52* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 7,875,265 B2 | 1/2011 | Blin et al. | |
| 8,119,110 B2 | 2/2012 | Blin et al. | |
| 8,586,013 B2 | 11/2013 | Bradshaw et al. | |
| 2006/0093568 A1 | 5/2006 | Blin et al. | |
| 2006/0115444 A1 | 6/2006 | Blin et al. | |
| 2006/0147402 A1 | 7/2006 | Blin et al. | |
| 2007/0134181 A1 | 6/2007 | Shimizu et al. | |
| 2008/0025934 A1 | 1/2008 | Lebre et al. | |
| 2009/0130037 A1 | 5/2009 | Thevenet et al. | |
| 2009/0214458 A1 | 8/2009 | Brun et al. | |
| 2010/0172852 A1* | 7/2010 | Favre et al. | 424/63 |
| 2010/0254933 A1* | 10/2010 | Favre et al. | 424/78.03 |
| 2010/0310489 A1* | 12/2010 | Barba | A61K 8/891 424/70.121 |
| 2011/0020263 A1 | 1/2011 | Ilekti et al. | |
| 2011/0243867 A1 | 10/2011 | Patel et al. | |
| 2011/0280817 A1 | 11/2011 | Ramadan et al. | |
| 2011/0293543 A1 | 12/2011 | Yu | |
| 2012/0171139 A1 | 7/2012 | Bradshaw et al. | |
| 2013/0171084 A1 | 7/2013 | Kawaratani et al. | |

FOREIGN PATENT DOCUMENTS

| | | |
|---|---|---|
| JP | 2010-513541 A | 4/2010 |
| JP | 2010-528085 A | 8/2010 |
| KR | 10 2009 0054540 | 6/2009 |

OTHER PUBLICATIONS

U.S. Appl. No. 14/354,719, filed Apr. 28, 2014, Bukawa, et al.
U.S. Appl. No. 14/359,791, filed May 21, 2014, Bui, et al.
International Search Report Issued Apr. 8, 2013 in PCT/US12/072052 Filed Dec. 28, 2012.
Office Action issued Jul. 28, 2015 in Japanese Patent Application No. 2014-550506 (with English language translation).
Office Action issued Sep. 3, 2015 in Korean Patent Application No. 10-2014-7018057.
Office Action as received in the corresponding Korean Patent Application No. 2014-7018057 dated Mar. 25, 2016 w/English Translation.

* cited by examiner

*Primary Examiner* — H. Sarah Park
(74) *Attorney, Agent, or Firm* — Oblon, McClelland, Maier & Neustadt, L.L.P.

(57) ABSTRACT

The invention relates to a composition, especially a cosmetic composition, comprising at least one silicon resin comprising at least one T unit, at least one phenylated oil and at least one gelling agent, as well as to methods of using such compositions.

13 Claims, No Drawings

COMPOSITIONS CONTAINING SILICON RESIN, OIL AND GELLING AGENT

CROSS-REFERENCE TO RELATED APPLICATIONS

This application claims the benefit of priority from U.S. Provisional Application Ser. No. 61/582,087, filed Dec. 30, 2011, the entire contents of which is hereby incorporated by reference.

FIELD OF THE INVENTION

The present invention relates to compositions comprising at least one silicon resin comprising at least one T unit, at least one phenylated oil and at least one gelling agent. Among other improved or beneficial properties, these compositions have surprisingly good stability, shine, wear, transfer-resistance, texture, and feel upon application properties.

DISCUSSION OF THE BACKGROUND

Many cosmetic compositions, including pigmented cosmetics such as foundations and lipsticks, have been formulated in an attempt to posses long wearing properties upon application. Unfortunately, many of these compositions do not generally possess both good long-wear/transfer-resistance properties and good application properties.

For example, commercial products containing silicon resins such as MQ resins are known. Such products are known to provide good long wear properties and/or transfer-resistance. However, such compositions possess poor application properties and poor feel upon application (owing to the film formed by the MQ resin).

Thus, there remains a need for improved cosmetic compositions having improved cosmetic properties, particularly good wear, feel, and texture characteristics upon application.

Accordingly, one aspect of the present invention is a care and/or makeup and/or treatment composition for keratinous materials which has good cosmetic properties such as, for example, good shine, feel, wear and/or texture properties upon application.

SUMMARY OF THE INVENTION

The present invention relates to compositions comprising at least one silicon resin comprising at least one T unit, at least one phenylated oil and at least one gellling agent. Preferably, the compositions are anhydrous and in the form of a stick.

The present invention also relates to colored compositions comprising at least one coloring agent, at least one silicon resin comprising at least one T unit, at least one phenylated oil and at least one gellling agent. Such colored compositions can be, for example, cosmetic compositions such as lip compositions (for example, lipstick) or foundations. Preferably, the compositions are anhydrous and in the form of a stick.

The present invention also relates to methods of treating, caring for and/or making up keratinous material (for example, skin or lips) by applying compositions of the present invention to the keratinous material in an amount sufficient to treat, care for and/or make up the keratinous material.

The present invention also relates to methods of enhancing the appearance of keratinous material (for example, skin or lips) by applying compositions of the present invention to the keratinous material in an amount sufficient to enhance the appearance of the keratinous material.

The present invention further relates to compositions having improved cosmetic properties such as, for example, increased stability, shine, increased anti-smudging properties, increased long wear properties, and/or better texture, and/or feel upon application. Preferably, the compositions are anhydrous and in the form of a stick.

The present invention also relates to methods of improving the stability, shine, feel, and/or texture properties of a composition upon application to a keratin material comprising adding to a composition (for example, a lip composition) at least one silicon resin comprising at least one T unit, at least one phenylated oil and at least one gellling agent.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to lips followed by rubbing a material, for example, a sheet of paper, against the lips after expiration of a certain amount of time following application, such as 2 minutes after application. Similarly, transfer resistance of a composition may be evaluated by the amount of product transferred from a wearer to any other substrate, such as transfer from the lips of an individual to a collar when putting on clothing after the expiration of a certain amount of time following application of the composition to the lips. The amount of composition transferred to the substrate (e.g., collar, or paper) may then be evaluated and compared. For example, a composition may be transfer resistant if a majority of the product is left on the wearer's lips. Further, the amount transferred may be compared with that transferred by other compositions, such as commercially available compositions. In a preferred embodiment of the present invention, little or no composition is transferred to the substrate from the lips.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to lips and evaluating the color of the composition after an extended period of time. For example, the color of a composition may be evaluated immediately following application to lips and these characteristics may then be re-evaluated and compared after a certain amount of time. Further, these characteristics may be evaluated with respect to other compositions, such as commercially available compositions.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100° C.

"Non-volatile", as used herein, means having a flash point of greater than about 100° C.

"Anhydrous" means the compositions contain less than 1% water. Preferably, the compositions of the present invention contain less than 0.5% water, and most preferably no water.

The composition of the present invention may be in any form, either liquid or non-liquid (semi-solid, soft solid, solid, etc.). For example, it may be a paste, a solid, a gel, or a cream. It may be an emulsion, such as an oil-in-water or water-in-oil emulsion, a multiple emulsion, such as an oil-in-water-in-oil emulsion or a water-in-oil-in-water emulsion, or a solid, rigid or supple gel. The composition of the invention may, for example, comprise an external or continuous fatty phase. The composition can also be a molded composition or cast as a stick or a dish.

Depending on the intended application, such as a stick, hardness of the composition may also be considered. The hardness of a composition may, for example, be expressed in gramforce (gf). The composition of the present invention may, for example, have a hardness ranging from 20 gf to 2000 gf, such as from 20 gf to 900 gf, and further such as from 20 gf to 600 gf.

This hardness is measured in one of two ways. A first test for hardness is according to a method of penetrating a probe into the composition and in particular using a texture analyzer (for example TA-XT2i from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 gf.

The second test for hardness is the "cheese wire" method, which involves cutting an 8.1 mm or preferably 12.7 mm in diameter stick composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 gf to 300 gf, such as from 30 gf to 250 gf, for a sample of 8.1 mm in diameter stick, and further such as from 30 gf to 200 gf, and also further such as from 30 gf to 120 gf for a sample of 12.7 mm in diameter stick.

The hardness of the composition of the present invention may be such that the compositions are self-supporting and can easily disintegrate to form a satisfactory deposit on keratin materials. In addition, this hardness may impart good impact strength to the inventive compositions, which may be molded or cast, for example, in stick or dish form.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within preferred embodiments of the invention.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 25° C., 37° C., 45° C. and under freeze-thaw conditions. A composition is considered to lack stability if in any of these tests an abnormality that impedes functioning of the composition is observed. The skilled artisan will readily recognize an abnormality that impedes functioning of a composition based on the intended application.

The cosmetic compositions and methods of the present invention can comprise, consist of, or consist essentially of the essential elements and limitations of the invention described herein, as well as any additional or optional ingredients, components, or limitations described herein or otherwise useful in personal care.

Silicone Resin Comprising at Least One T Unit

According to the present invention, compositions comprising at least one silicon resin comprising at least one T unit are provided. Suitable silicone resins in accordance with the present invention are disclosed, for example, in U.S. patent applications 2007/0166271, 2011/0038820, 2011/0002869, and 2009/0214458, the entire contents of which are hereby incorporated by reference in their entirety.

As used herein, the term "resin" means a crosslinked or non-crosslinked three-dimensional structure. Examples of polysiloxane T resins that may be mentioned include silsesquioxanes and siloxysilicates.

The nomenclature of silicone resins is known under the name MDTQ, the resin being described as a function of the various siloxane monomer units it comprises, each of the letters MDTQ characterizing a type of unit.

The letter M represents the monofunctional unit, for example, of formula $(CH_3)_3SiO_{1/2}$, the silicon atom being connected to only one oxygen atom in the polymer comprising this unit.

The letter D means a difunctional unit, for example, $(CH_3)_2SiO_{2/2}$ in which the silicon atom is connected to two oxygen atoms.

The letter T represents a trifunctional unit, for example, of formula $(CH_3)SiO_{3/2}$.

In the M, D and T units listed as examples above, at least one of the methyl groups may be substituted. In some embodiments, the at least one silicone resin comprising at least one trifunctional unit of formula $(R)SiO_{3/2}$ is chosen from the silsesquioxanes of formula: $((R)SiO_{3/2})_x$, in which x ranges from 100 to 500 and R' is chosen, independently by trifunctional unit, from a hydrocarbon-based group containing from 1 to 10 carbon atoms or a hydroxyl group, on the condition that at least one R' is a hydrocarbon-based group. In some embodiments, the hydrocarbon-based group containing from 1 to 10 carbon atoms is a methyl group. In some embodiments, the at least one silicone resin comprising at least one trifunctional unit of formula $(R)SiO_{3/2}$ is chosen from the silsesquioxanes of the formula: $((R)SiO_{3/2})_x$, in which x ranges from 100 to 500 and R' is chosen, independently by unit, from $CH_3$, a hydrocarbon-based group containing from 2 to 10 carbon atoms, or a hydroxyl group, on the condition that at least one R' is a hydrocarbon-based group.

Finally, the letter Q means a tetrafunctional unit $SiO_{4/2}$ in which the silicon atom is bonded to four hydrogen atoms, which are themselves bonded to the rest of the polymer.

Various resins with different properties may be obtained from these different units, the properties of these polymers varying as a function of the type of monomers (or units), of the type and number of substituted groups, of the length of the polymer chain, of the degree of branching and of the size of the side chains.

The silicone resin contains at least one T unit. It may thus be, for example, a T, MT, MTQ or MDTQ resin.

In some embodiments, the unit composition of the silicone resin is at least 50% T units, or at least 70% T units, or at least 80% T units, or at least 90% T units.

In some embodiments, the T resins may contain M, D and Q units such that at least 80 mol % or at least 90 mol %, relative to the total amount of silicones, are T units. The T resins may also contain hydroxyl and/or alkoxy groups. The T resins may have a total weight of hydroxyl functions ranging from 2% to 10% and a total weight of alkoxy functions that may be up to 20%; in some embodiments, the total weight of hydroxyl functions ranges from 4% to 8% and the total weight of alkoxy functions may be up to 10%.

The silicone resin may be chosen from silsesquioxanes that are represented by the following formula: $((CH_3)SiO_{3/2})_x$, in which x may be up to several thousand and the $CH_3$ group may be replaced with an R group, as described previously in the definition of the T units. The number x of T units of the silsesquioxane may be less than or equal to 500, or it may range from 50 to 500, including all ranges and subranges therebetween. The molecular weight of the silicone resin may range from 500 to 50,000 g/mol, from 500 to 20,000 g/mol, or from 500 to 10,000 g/mol, including all ranges and subranges therebetween.

The silicone resin may be film-forming. Specifically, not all silsesquioxanes are film-forming: for example, highly polymerized polymethylsilsesquioxanes such as Tospearl™ from Toshiba or KMP590 from Shin-Etsu are insoluble and are not film-forming. The molecular weight of these polymethylsilsesquioxanes is difficult to determine, but there are generally more than 1000 T units.

As suitable examples of these silicone resins containing at least one T unit, mention may be made of:

polysilsesquioxanes of formula $((R)SiO_{3/2})_x$ (T units) in which x is greater than 100, in which the R groups may independently be methyl or other substituents as defined above;

polymethylsilsesquioxanes, which are polysilsesquioxanes in which R is a methyl group. Such polymethylsilsesquioxanes are described, for example, in U.S. Pat. No. 5,246,694, the entire contents of which is hereby incorporated by reference in its entirety;

polypropylsilsesquioxanes, in which R is a propyl group. These compounds and their synthesis are described, for example, in patent application WO 2005/075567, the entire contents of which is hereby incorporated by reference in its entirety;

polyphenylsilsesquioxanes, in which R is a phenyl group. These compounds and their synthesis are described, for example, in patent application US 2004/0180011, the entire contents of which is hereby incorporated by reference in its entirety.

Examples of commercially available polymethylsilsesquioxane resins that may be mentioned include those sold:

by the company Wacker under the reference Resin MK such as Belsil PMS MK: polymer comprising $CH_3SiO_{3/2}$ repeating units (T units), which may also comprise up to 1% by weight of $(CH_3)_2SiO_{2/2}$ units (D units) and having an average molecular weight of about 10 000 g/mol. It is thought that the polymer is in a "cage" and "ladder" configuration as represented in the figures below. The average molecular weight of the units in "cage" configuration has been calculated as 536 g/mol. The majority of the polymer is in the "ladder" configuration with ethoxy groups at the ends. These ethoxy groups represent 4.5% by mass of the polymer. As these end groups can react with water, a small and variable amount of SiOH groups may also be present;

by the company Shin-Etsu under the references KR-220L, which are composed of T units of formula $CH_3SiO_{3/2}$ and have Si—OH (silanol) end groups, under the reference KR-242A, which comprise 98% of T units and 2% of dimethyl D units and have Si—OH end groups or alternatively under the reference KR-251 comprising 88% of T units and 12% of dimethyl D units and have Si—OH end groups.

Examples of commercially available polypropylsilsesquioxane resins that may be mentioned include those sold:

by the company Dow Corning under the reference Dow Corning 670 Fluid, which is a polypropylsilsesquioxane diluted in volatile oil such as volatile hydrocarbon oil or volatile silicone oil such as D5.

Examples of commercially available polyphenylsilsesquioxane resins that may be mentioned include those sold:

by the company Dow Corning under the reference Dow Corning 217 Flake Resin, which is a polyphenylsilsesquioxane with silanol end groups;

by the company Wacker under the reference Belsil SPR 45 VP.

In the composition of the present invention, the silicon resin(s) comprising at least one T unit is/are preferably present in an amount of from about 0.5 to about 50 percent by weight, more preferably from 1 to 30 percent by weight, more preferably from 5 to 30 percent by weight and most preferably from 10 to 20 percent by weight of the total weight of the composition, including all ranges and subranges therebetween.

Phenylated Oil

According to the present invention, compositions comprising at least one phenylated oil are provided. Preferably, the phenylated oil is selected from the group consisting of phenyl ester oils, phenyl silicone oils, and mixtures thereof.

Suitable phenyl ester oils include, but are not limited to, oils comprising at least one phenyl group and at least one ester group. Preferably, phenyl ester oils of the present invention have a melting point below 20° C. Specific examples of suitable phenyl ester oils include alkyl or aryl benzoates, in particular C8 to C18 alkyl benzoates, in particular C12 to C15 alkyl benzoates, in particular C12 to C14 alkyl benzoates, or benzyl benzoates. Commercially available examples of a suitable phenyl esters are those available under the trademark Finsolv® and those commercially available from Evonik Goldschmidt under the tradename Tegosoft® TN.

Suitable phenyl silicone oils include, but are not limited to, organopolysiloxanes substituted with at least one phenyl group. Of course, the oil can contain more than one phenyl group such as, for example, two phenyl groups, three phenyl groups, four phenyl groups, five phenyl groups, six phenyl groups, etc. The phenyl silicone is preferably non-volatile. Preferably, the weight-average molecular weight of the phenyl silicone oil is between 500 and 10 000 g/mol. Suitable such oils are disclosed in U.S. patent application 2010/0038820, the entire contents of which are hereby incorporated by reference.

Examples of phenyl silicone oils include, but are not limited to, phenyl trimethicones, phenyl dimethicones, phenyltrimethylsiloxydiphenylsiloxanes, trimethylsiloxyphenylsiloxanes, diphenyl dimethicones, diphenyl methyldiphenyl trisiloxanes, 2-phenylethyl trimethylsiloxysilicates, triphenyl, tetraphenyl or pentaphenyl organopolysiloxanes.

Commercially available examples of such phenyl ester oils include phenyl silicone manufactured by Dow Corning under the reference Dow Corning 555 Cosmetic Fluid (INCI name: trimethyl pentaphenyl trisiloxane), phenyl trimethicones such as DC556 from Dow Corning (22.5 cSt), Silbione 70663V30 from Rhone Poulenc (28 cSt) and diphenyl dimethicones such as Belsil oils, especially Belsil PDM1000 (1000 cSt), Belsil PDM 200 (200 cSt) and Belsil PDM 20 (20 cSt) from Wacker.

According to preferred embodiments, compositions of the present invention comprise the at least one oil in an amount of 0.5% to 70% by weight, preferably 2.5% to 50%, preferably from 5% to 40% by weight relative to the total weight of the composition.

Gelling Agent

According to the present invention, compositions comprising at least one gelling agent are provided. Preferably, the gelling agent is selected from the group consisting of glyceryl esters, silicas, waxes, and mixtures thereof.

Suitable glyceryl esters include, but are not limited to, hydrogenated glyceride compounds such as, for example, hydrogenated palm glycerides, hydrogenated palm kernel glycerides, hydrogenated soy glycerides, hydrogenated vegetable glycerides, hydrogenated rapeseed glycerides, hydrogenated coco-glycerides, hydrogenated cotton glycerides, hydrogenated cotton glycerides, and mixtures thereof. A commercially available example of a suitable glyceryl ester is hydrogenated palm kernel glycerides, commercially available as a mixture from Gattefosse under the tradename Lipocire® DM.

Suitable silicas include, but are not limited to, hydrophobic silicas, such as pyrogenic silica optionally with hydrophobic surface treatment whose particle size is less than 1 micron. It is in fact possible to modify the surface of silica chemically, by a chemical reaction producing a decrease in the number of silanol groups present on the surface of the silica. The silanol groups can notably be replaced with hydrophobic groups: a hydrophobic silica is then obtained. The hydrophobic groups can be:

trimethylsiloxyl groups, which are notably obtained by treatment of pyrogenic silica in the presence of hexamethyldisilazane. Silicas treated in this way are called "Silica silylate" according to the CTFA (6th edition, 1995). They are for example marketed under the references "AEROSIL R812®" by the company Degussa, "CAB-O-SIL TS-530®" by the company Cabot;

dimethylsilyloxyl or polydimethylsiloxane groups, which are notably obtained by treatment of pyrogenic silica in the presence of polydimethylsiloxane or dimethyldichlorosilane. Silicas treated in this way are called "Silica dimethyl silylate" according to the CTFA (6th edition, 1995). They are for example marketed under the references "AEROSIL R972®", "AEROSIL R974 ®" by the company Degussa, "CAB-O-SIL TS-610®", "CAB-O-SIL TS-720®" by the company Cabot.

Hydrophobic pyrogenic silica preferably has a particle size that can be nanometric to micrometric, for example in the range from about of 5 to 200 nm.

Suitable examples of waxes that can be used in accordance with the present disclosure include those generally used in the cosmetics field: they include those of natural origin, such as beeswax, carnauba wax, candelilla wax, ouricoury wax, Japan wax, cork fibre wax or sugar cane wax, rice wax, montan wax, paraffin wax, lignite wax or microcrystalline wax, ceresin or ozokerite, and hydrogenated oils such as hydrogenated castor oil or jojoba oil; synthetic waxes such as the polyethylene waxes obtained from the polymerization or copolymerization of ethylene, and Fischer-Tropsch waxes, or else esters of fatty acids, such as octacosanyl stearate, glycerides which are concrete at 30° C., for example at 45° C.

According to particularly preferred embodiments of the present invention, the compositions of the present invention comprise at least one silicone wax. Examples of suitable silicone waxes include, but are not limited to, silicone waxes such as alkyl- or alkoxydimethicones having an alkyl or alkoxy chain ranging from 10 to 45 carbon atoms, poly(di) methylsiloxane esters which are solid at 30° C. and whose ester chain comprising at least 10 carbon atoms, di(1,1,1-trimethylolpropane) tetrastearate, which is sold or manufactured by Heterene under the name HEST 2T-4S; silicone resin waxes comprising at least 40 mole % of siloxy units having the formula $(R_2R'SiO_{1/2})_x(R''SiO_{3/2})_y$, where x and y have a value of 0.05 to 0.95, R is an alkyl group having from 1 to 8 carbon atoms, an aryl group, a carbinol group, or an amino group, R is a monovalent hydrocarbon having 9-40 carbon atoms, R" is a monovalent hydrocarbon group having 1 to 8 carbon atoms, an aryl group such as those disclosed in U.S. patent application 2007/0149703, the entire contents of which is hereby incorporated by reference, with a particular example being C30-C45 alkyldimethylsilyl polypropylsilsesquioxane; and mixtures thereof.

According to preferred embodiments, when the compositions of the present invention are in the form of a lip gloss, the gelling agent preferably has a particle size of at least one micron, with the upper limit being that of the larger gelling agents identified herein.

According to preferred embodiments, compositions of the present invention comprise the at least one gelling agent in an amount of 0.5% to 20% by weight, preferably 2.5% to 15%, preferably from 5% to 10% by weight relative to the total weight of the composition.

Oil Phase

In addition to the oil(s) identified above, the compositions of the present invention can further comprise, if desired, additional oil(s). "Oil" means any non-aqueous medium which is liquid at ambient temperature (25° C.) and atmospheric pressure (760 mm Hg). A "wax" for the purposes of the present disclosure is a lipophilic fatty compound that is solid at ambient temperature (25° C.) and changes from the solid to the liquid state reversibly, having a melting temperature of more than 30° C. and, for example, more than 45° C., which can be as high as 150° C., a hardness of more than 0.5 MPa at ambient temperature, and an anisotropic crystalline organization in the solid state.

Suitable oils include volatile and/or non-volatile oils. Such oils can be any acceptable oil including but not limited to silicone oils and/or hydrocarbon oils.

According to certain embodiments, the composition of the present invention preferably comprise one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, a volatile linear silicone oil may be employed in the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to certain embodiments of the present invention, the composition of preferably comprises one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isohexacecane, isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
|---|---|
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatility of the solvents/oils can be determined using the evaporation speed as set forth in U.S. Pat. No. 6,338,839, the contents of which are incorporated by reference herein.

According to certain embodiments of the present invention, the composition comprises at least one non-volatile oil.

Examples of non-volatile oils that may be used in the present invention include, but are not limited to, polar oils such as:
hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;
synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, octyldodecyl neopentanoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;
synthetic ethers containing from 10 to 40 carbon atoms;
$C_8$ to $C_{26}$ fatty alcohols, for instance oleyl alcohol, cetyl alcohol, stearyl alcohol, and cetearly alcohol; and
mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

According to certain embodiments of the present invention, the compositions of the present invention comprise at least one silicone oil. Suitable examples of such silicone oils include, but are not limited to, non-volatile silicone fluids such as, for example, polyalkyl (aryl) siloxanes. Suitable polyalkyl siloxanes include, but are not limited to, polydimethyl siloxanes, which have the CTFA designation dimethicone.

According to preferred embodiments, the at least one oil is present in the compositions of the present invention in an amount ranging from about 5 to about 60% by weight, more preferably from about 10 to about 50% by weight, and most preferably from about 15 to about 35% by weight, based on the total weight of the composition, including all ranges and subranges within these ranges.

According to particularly preferred embodiments, the compositions of the present invention, at least one volatile oil and at least one non-volatile oil are present. In accordance with these preferred embodiments, the at least one volatile oil is present in the compositions of the present invention in an amount ranging from about 5 to about 50% by weight, preferably from about 10 to about 40% by weight, and preferably from about 12 to about 37% by weight, based on the total weight of the composition, including all ranges and subranges within these ranges, and the at least one non-volatile oil is present in the compositions of the present invention in an amount ranging from about 10 to about 50% by weight, preferably from about 12 to about 45% by weight, and preferably from about 15 to about 40% by weight, based on the total weight of the composition, including all ranges and subranges within these ranges.

Coloring Agents

According to preferred embodiments of the present invention, compositions further comprising at least one coloring agent are provided. Preferably, such colored compositions can be cosmetic compositions such as, for example, lip compositions (for example, lipstick) or foundations.

According to this embodiment, the at least one coloring agent is preferably chosen from pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%, including all ranges and subranges therebetween.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.1% to 20%, preferably from 0.1% to 15%, including all ranges and subranges therebetween.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the coloring agents may be present in the composition in a concentration ranging up to 50% by weight of the total weight of the composition, such as from 0.5% to 40%, and further such as from 2% to 30%, including all ranges and subranges therebetween. In the case of certain products, the pigments, including nacreous pigments, may, for example, represent up to 50% by weight of the composition.

Additional Additives

The composition of the invention can also comprise any additive usually used in the field under consideration. For example, dispersants such as poly(12-hydroxystearic acid), antioxidants, film forming agents, essential oils, sunscreens, preserving agents, fragrances, fillers, neutralizing agents, cosmetic and dermatological active agents such as, for example, emollients, moisturizers, vitamins, essential fatty acids, surfactants, silicone elastomers, pasty compounds, viscosity increasing agents such as waxes or liposoluble/lipodispersible polymers, and mixtures thereof can be added. A non-exhaustive listing of such ingredients can be found in U.S. patent application publication no. 2004/0170586, the entire contents of which is hereby incorporated by reference.

Further examples of suitable additional components can be found in the other references which have been incorporated by reference in this application. Still further examples of such additional ingredients may be found in the *International Cosmetic Ingredient Dictionary and Handbook* ($9^{th}$ ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable medium and should be able to be applied to the eyelashes of human beings.

According to preferred embodiments of the present invention, methods of treating, caring for and/or making up keratinous material such as skin and lips by applying compositions of the present invention to the keratinous material in an amount sufficient to treat, care for and/or make up the keratinous material are provided. Preferably, "making up" the keratin material includes applying at least one coloring agent to the keratin material in an amount sufficient to provide color to the keratin material.

According to yet other preferred embodiments, methods of enhancing the appearance of keratinous material by applying compositions of the present invention to the keratinous material in an amount sufficient to enhance the appearance of the keratinous material are provided.

In accordance with the preceding preferred embodiments, the compositions of the present invention are applied topically to the desired area of the keratin material in an amount sufficient to treat, care for and/or make up the keratinous material, to cover or hide defects associated with keratinous material, skin imperfections or discolorations, or to enhance the appearance of keratinous material. The compositions may be applied to the desired area as needed, preferably once or twice daily, more preferably once daily and then preferably allowed to dry before subjecting to contact such as with clothing or other objects (for example, a glass or a topcoat). Preferably, the composition is allowed to dry for about 1 minute or less, more preferably for about 45 seconds or less. The composition is preferably applied to the desired area that is dry or has been dried prior to application, or to which a basecoat has been previously applied.

According to a preferred embodiment of the present invention, compositions having improved cosmetic properties such as, for example, improved feel upon application (for example, texture, reduced drag, spreadability, and/or reduced tackiness), improved shine (initial shine after application and shine 1 hour after application), increased anti-smudging properties, increased stability and/or increased long wear properties are provided.

According to other embodiments of the present invention, methods of improving the stability, anti-smudging, transfer-resistance, adherence, shine (initial shine after application and shine 1 hour after application) and/or long wear properties of a composition, comprising adding at least one silicon resin comprising at least one T unit, at least one phenylated oil and at least one gelling agent are provided.

According to further embodiments of the present invention, methods of improving the feel or texture of a composition, preferably a makeup compositions such as a foundation or lip composition, comprising adding at least one silicon resin comprising at least one T unit, at least one phenylated oil and at least one gelling agent are provided.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Methodology—Determination of Shine

For purposes of this application, shine is calculated to be the difference between the parallel polarized and cross polarized images taken at specified time intervals such as 0 hours, after 1 hour, and after eating (a baseline image of lips prior to application can also be taken). 5% of the brightest pixels of the difference image is reported as shine value. Shine values are unitless.

Methodology—Determination of Wear

For purposes of this application, the wear score is based on a 100% point scale (a maximum of 50% for the upper lip, and a maximum of 50% for the lower lip). For example, if a subject's score is 65%, 65% of the product remains on the lips combined.

Wear is determined as follows:

After cleaning lips, a baseline image of the lips is taken. Then, two (2) even coats of lip product is applied and a picture image is taken (t=0 hours). Subjects then consume drinks using a straw during the day. Then, after a designated number of hours (such as two or four hours), subjects can eat nongreasy/oily foods and record the items eaten on a diary, if desired. Whether or not eating has occurred, pictures can be taken at such time intervals. After 8 hours, a final picture image is taken.

To determine the wear scores, median scores are calculated. The grading scale for lipstick wear is as follows:

0=no color

1=slight color

2=moderate color

3=initial application

For a product to be considered to "wear" at a designated number of hours after application, the median score should be at least 2 for the designated time period.

Compositions—The following compositions were prepared and evaluated:

Example 1

Lipstick

| | |
|---|---|
| Polypropylsilsesquioxane (and) isododecane | 36.4% |
| Trimethylsiloxyphenyl dimethicone | 34.5% |
| Hydrogenated palm kernel glycerides (and) hydrogenated palm glycerides | 3% |
| C12-15 alkyl benzoate | 3% |
| Stearyl heptanoate | 2% |
| Silica | 0.5% |
| Ozokerite | 2% |
| Lauroyl Lysine | 0.2% |
| Silica dimethyl silylate | 2% |
| Isododecane | 1.9% |
| Titanium dioxide | 2.74% |
| Blue 1 lake | 0.16% |
| Yellow 6 lake | 2.58% |
| Red 7 | 0.59% |
| Iron oxides | 0.32% |
| Mica (and) titanium dioxide (and) iron oxides | 2% |
| Mica | 5.61% |
| Fragrance | 0.5% |

Example 2

Lip Gloss

| | |
|---|---|
| Polypropylsilsesquioxane (and) isododecane | 40.0% |
| Trimethylsiloxyphenyl dimethicone | 21% |
| Hydrogenated Styrene/Methyl Styrene/Indene Copolymer | 7.50% |
| Hydrogenated palm kernel glycerides (and) hydrogenated palm glycerides | 1% |
| C12-15 alkyl benzoate | 3.5% |
| Stearyl heptanoate | 7% |
| C30-45 AlkylDimethylSilyl Polypropylsilsesquioxane (and) Paraffin | 2.5% |
| Ozokerite | 2% |
| Isododecane | 5.5% |
| Titanium dioxide | 0.67% |
| Red 28 | 4.79% |
| Yellow 6 lake | 0.82% |
| Red 7 | 1.72% |
| Mica | 2.0% |

| | Immediate Shine | Shine 1 Hr | Shine 2 Hr |
|---|---|---|---|
| Shine Testing | 172.7 (±7.1) | 168.2 (±10.0) | 162.7 (±18.9) |

| | Sample Size | % Wear after Classic Meal Test | Immediate Shine | Shine 1 Hr |
|---|---|---|---|---|
| Wear Testing | 6 | 46.8 (±7.2) | 159.4 (±15.4) | 153.6 (±17.9) |

Example 3

Lip Gloss

| | |
|---|---|
| Polypropylsilsesquioxane (and) isododecane | 40.0% |
| Hydrogenated Styrene/Methyl Styrene/Indene Copolymer | 0.5% |
| Trimethylsiloxyphenyl dimethicone | 20.79% |
| Polybutene | 15.0% |
| Trimethyl Pentaphenyl Trisiloxane | 5.0% |
| Lauryl Peg-9 Polydimethyl Siloxyethyl Dimethicone | 5.0% |
| Trihydroxystearin | 1.5% |
| Synthetic Wax | 1.5% |
| C30-45 AlkylDimethylSilyl Polypropylsilsesquioxane (and) Paraffin | 2.0% |
| Titanium dioxide | 0.34% |
| Red 28 | 2.4% |
| Yellow 6 lake | 0.41% |
| Red 7 | 0.86% |
| Mica | 4.0% |
| Fragrance | 0.70% |

| Wear Scores - Time Points | Sample Size | Median Scores (25%-75%) |
|---|---|---|
| Baseline | 26 | 0.00 (0.00-0.00) |
| Initial | 26 | 3.00 (3.00-3.00) |
| Eight (8) Hours Post-Application | 26 | 2.00 (2.00-2.00) |

Example 4

Lip Gloss

| | |
|---|---|
| Polypropylsilsesquioxane (and) isododecane | 40.0% |
| Hydrogenated Styrene/Methyl Styrene/Indene Copolymer | 2.5% |
| Hydrogenated Polycyclopentadiene | 8.0% |
| Trimethylsiloxyphenyl dimethicone | 17.72% |
| Polyglyceryl-4 Isostearate (and) Cetyl PEG/PPG-10/1 Dimethicone (and) Hexyl Laurate | 9.0% |
| Polybutene | 10.0% |
| Beeswax | 2.5% |
| Synthetic Beeswax | 2.5% |
| C30-45 AlkylDimethylSilyl Polypropylsilsesquioxane (and) Paraffin | 1.0% |
| Titanium dioxide | 0.34% |
| Red 28 | 2.4% |
| Yellow 6 lake | 0.41% |
| Red 7 | 0.86% |
| Mica | 2.27% |
| Fragrance | 0.50% |

| Wear Scores - Time Points | Sample Size | Median Scores (25%-75%) |
|---|---|---|
| Baseline | 12 | 0.00 (0.00-0.00) |
| Initial | 12 | 3.00 (3.00-3.00) |
| Eight (8) Hours | 12 | 2.00 (2.00-2.00) |

What is claimed is:

1. A composition, comprising a polypropylsilsesquioxane film former in an amount of 1 to 30% by weight of the composition, trimethylsiloxyphenyl dimethicone and $C_{12}$-$C_{15}$ alkyl benzoate in a total amount of 2.5 to 50% by weight of the composition, and a gelling agent in an amount of 2.5 to 15% by weight of the composition.

2. The composition of claim 1, wherein the gelling agent is a wax.

3. The composition of claim 1, wherein the gelling agent is a hydrophobic silica.

4. The composition of claim 1, wherein the gelling agent is a glyceryl ester.

5. The composition of claim 1, further comprising at least one coloring agent.

6. The composition of claim 1, further comprising at least one volatile oil.

7. The composition of claim 1, in the form of a stick.

8. The composition of claim 1, wherein the composition is anhydrous.

9. A method of making up lips comprising applying the composition of claim 1 to the lips.

10. A method of making up skin comprising applying the composition of claim 1 to the skin.

11. The composition of claim 1, comprising the polypropylsilsesquioxane film former in an amount of 10 to 20 percent by weight of the composition, the trimethylsiloxyphenyl dimethicone and C12-15 alkyl benzoate in a total amount of 5 to 40% by weight of the composition, and the gelling agent in an amount of 5 to 10% by weight of the composition.

12. The composition of claim 11, which is anhydrous and in the form of a stick.

13. A method of making up lips comprising applying the composition of claim 12 to the lips.

* * * * *